United States Patent
Shen et al.

(10) Patent No.: US 10,517,523 B2
(45) Date of Patent: Dec. 31, 2019

(54) SKIN AGING STATE ASSESSMENT METHOD AND ELECTRONIC DEVICE

(71) Applicant: CAL-COMP BIG DATA, INC., New Taipei (TW)

(72) Inventors: Shyh-Yong Shen, New Taipei (TW); Min-Chang Chi, New Taipei (TW); Yung-Hsuan Lin, New Taipei (TW); Ching-Wei Wang, New Taipei (TW)

(73) Assignee: CAL-COMP BIG DATA, INC., New Taipei (TW)

( * ) Notice: Subject to any disclaimer, the term of this patent is extended or adjusted under 35 U.S.C. 154(b) by 217 days.

(21) Appl. No.: 15/814,400

(22) Filed: Nov. 16, 2017

(65) Prior Publication Data

US 2019/0059806 A1    Feb. 28, 2019

(30) Foreign Application Priority Data

Aug. 31, 2017 (CN) .......................... 2017 1 0768329

(51) Int. Cl.
*A61B 5/00* (2006.01)
*G06T 7/00* (2017.01)
*G06K 9/00* (2006.01)

(52) U.S. Cl.
CPC .............. *A61B 5/442* (2013.01); *A61B 5/444* (2013.01); *G06T 7/0016* (2013.01); *G06K 2009/00322* (2013.01)

(58) Field of Classification Search
CPC ....... G06T 7/00; G06T 7/0012; G06T 7/0014; G06T 7/0016; G06T 7/97; G06T 2207/30088; G06T 2207/30201; G06K 9/00221; G06K 9/00248; G06K 9/00281; G06K 2009/00322; A61B 5/441; A61B 5/442; A61B 5/444

See application file for complete search history.

(56) References Cited

U.S. PATENT DOCUMENTS

| 2013/0121584 | A1 | 5/2013 | Bourdev et al. | |
| 2014/0099029 | A1* | 4/2014 | Savvides et al. | G06K 9/481 382/197 |
| 2015/0099947 | A1* | 4/2015 | Qu et al. | A61B 5/442 600/306 |
| 2015/0116471 | A1 | 4/2015 | Chang | |
| 2018/0035942 | A1* | 2/2018 | Lee et al. | A61B 5/0075 |

FOREIGN PATENT DOCUMENTS

WO    2011065952 A1    6/2011

OTHER PUBLICATIONS

"Search Report of Europe Counterpart Application", dated Mar. 8, 2018, pp. 1-9.

\* cited by examiner

*Primary Examiner* — Andrew W Johns
(74) *Attorney, Agent, or Firm* — JCIPRNET (57) ABSTRACT

The invention provides a skin aging state assessment method and an electronic device. The method includes: acquiring a first image and a second image; acquiring a characteristic parameter of the first image and a characteristic parameter of the second image; acquiring an aging parameter according to the characteristic parameter of the first image and the characteristic parameter of the second image; and deciding an aging assessment result corresponding to the first image according to the aging parameter. The skin state detection method of the invention makes it possible to use two face images captured at different times to acquire the skin aging condition of the face images.

20 Claims, 4 Drawing Sheets

SKIN AGING STATE ASSESSMENT METHOD AND ELECTRONIC DEVICE

CROSS-REFERENCE TO RELATED APPLICATION

This application claims the priority benefit of Chinese application serial no. 201710768329.6, filed on Aug. 31, 2017. The entirety of the above-mentioned patent application is hereby incorporated by reference herein and made a part of this specification.

BACKGROUND OF THE INVENTION

Field of the Invention

The invention relates to a skin detection technique and more particularly relates to a skin aging state assessment method and an electronic device.

Description of Related Art

The traditional skin detection is usually performed by using a professional skin detector to scan people's skin, so as to determine the skin condition. Manufacturers' sales staff may recommend suitable skincare products according to the skin condition to promote their products. However, it is not easy for the user to buy a professional skin detector for personal use. The reason is that such a skin detector is expensive and large in size. Besides, the skin detector is equipped with different microscope lenses so as to scan the skin for capturing images at different magnifications. Since only a small area of the skin is scanned each time, operation of the skin detector will take a long time. Also, it requires professional training to learn how to assess the skin condition through the skin detector. Therefore, for users who want to frequently check whether the skin condition has improved, the skin detector may not be an ideal option.

In addition, skin will gradually age with time, but the general users cannot effectively and accurately know the skin condition. For these reasons, how to effectively and accurately know the skin aging condition is an issue that needs to be addressed in the field.

SUMMARY OF THE INVENTION

The invention provides a skin state detection method, by which two face images captured at different times are used to acquire a skin aging condition of the face images.

The invention provides a skin aging state assessment method. The method includes: acquiring a first image and a second image; acquiring a characteristic parameter of the first image and a characteristic parameter of the second image; acquiring an aging parameter according to the characteristic parameter of the first image and the characteristic parameter of the second image; and deciding an aging assessment result corresponding to the first image according to the aging parameter.

The invention provides an electronic device. The electronic device includes a storage device and a processor. The storage device stores a plurality of modules. The processor is coupled to the storage device and accesses and executes the modules stored in the storage device. The modules include an image acquisition module, a characteristic parameter acquisition module, and an aging assessment module. The image acquisition module acquires a first image and a second image. The characteristic parameter acquisition module acquires a characteristic parameter of the first image and a characteristic parameter of the second image. The aging assessment module acquires an aging parameter according to the characteristic parameter of the first image and the characteristic parameter of the second image, and decides an aging assessment result corresponding to the first image according to the aging parameter.

Based on the above, in the skin aging state assessment method of the invention, the skin aging parameter of the user is acquired according to two images captured at different times, and the skin aging assessment result of the user is decided according to the skin aging parameter, for the user to know the skin aging condition.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
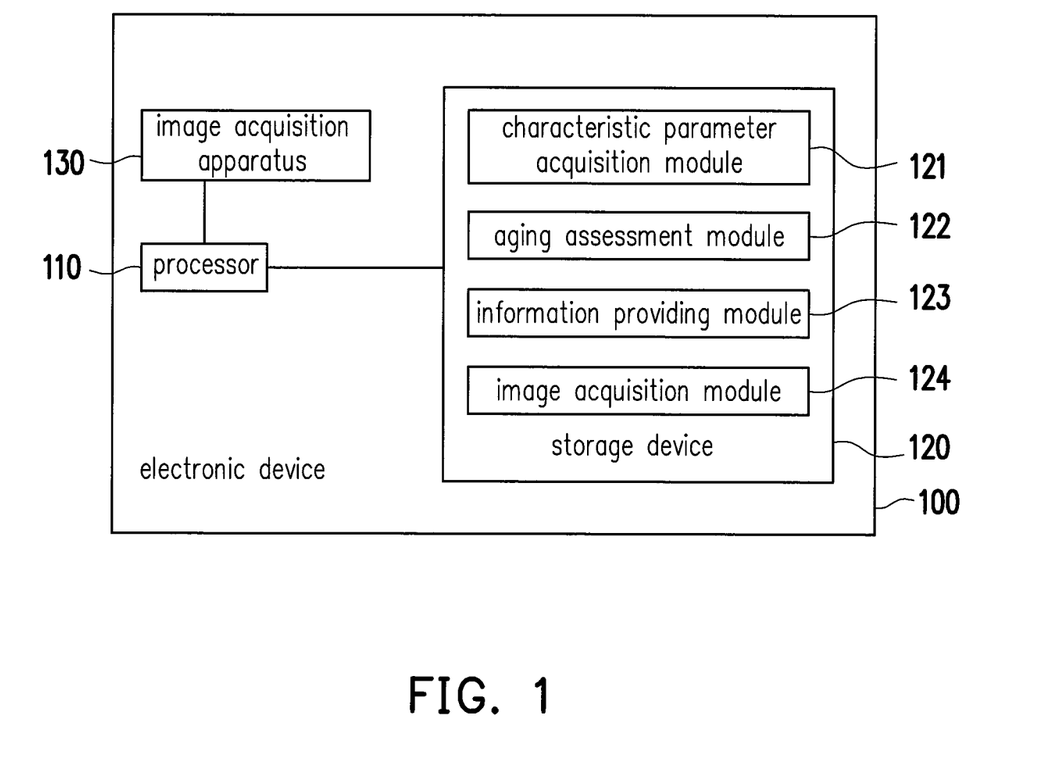
FIG. 1 is a schematic diagram of an electronic device according to an embodiment of the invention.

FIG. 1 is a schematic diagram of an electronic device according to an embodiment of the invention. Referring to FIG. 1, an electronic device 100 of this embodiment at least includes a processor 110 and a storage device 120, wherein the processor 110 is coupled to the storage device 120. In an embodiment, the electronic device 100 may further include an image acquisition apparatus 130, wherein the processor 110 is coupled to the image acquisition apparatus 130. The electronic device 100 described in the embodiment of the invention may be disposed on a mirror of a dressing table for acquiring and analyzing a skin image of the user to assess a skin aging condition of the user when the user is looking in the mirror, and providing information related to a skin aging assessment result by a display (not shown) disposed behind the mirror. It should be noted that, in other embodiments, the electronic device 100 may be an electronic product, such as a smartphone, a tablet computer, and a desktop computer, or a portable mirror case with a portable mirror.

The processor 110 may be a central processing unit (CPU), a microprocessor, a digital signal processor, a programmable controller, an application specific integrated circuit (ASIC), a programmable logic device (PLD), or other devices with data computing functions.

The storage device 120 may be any type of fixed or portable random access memory (RAM), read-only memory (ROM), flash memory, similar devices, or a combination of the foregoing. In this embodiment, the storage device 120 is configured to record a characteristic parameter acquisition module 121, an aging assessment module 122, an information providing module 123, and an image acquisition module 124. The modules are for example computer programs stored in the storage device 120, which may be loaded to the processor 110 for the processor 110 to execute functions of the skin aging state assessment method of the embodiment of the invention. It should be noted that the storage device 120 described in the above embodiment is not necessarily one single memory device, and the modules may also be separately stored in two or more memory devices, which may be of the same or different types. In other embodiments of the invention, the modules may be implemented by specific circuit structures respectively, for example. Steps of the method are described in detail in the following embodiment.

The image acquisition apparatus 130 may be a camera equipped with a charge coupled device (CCD), a complementary metal-oxide semiconductor (CMOS) device, or other types of photosensitive devices, and may be configured to acquire a skin image of the user, especially face and neck skin images.

In an embodiment of the invention, the electronic device 100 further includes components, such as an input/output interface (not shown), a communication interface (not shown), and so on, but the invention is not limited thereto. More specifically, the input/output interface includes components, such as a display, a speaker, a keyboard, a mouse, a touch panel, and so on, for outputting or inputting information and data. The communication interface supports various wired communication standards and wireless communication standards for the electronic device 100 to connect with other devices.

The skin aging state assessment method provided in the embodiment of the invention is applicable to the electronic device 100 as shown in FIG. 1. The skin aging state assessment method is described in the following embodiment with reference to the electronic device 100 as shown in FIG. 1. However, it should be noted that the skin aging state assessment method is not necessarily used on the electronic device 100. Other electronic devices or systems with corresponding capabilities may also perform the skin aging state assessment method.

Figure 2:
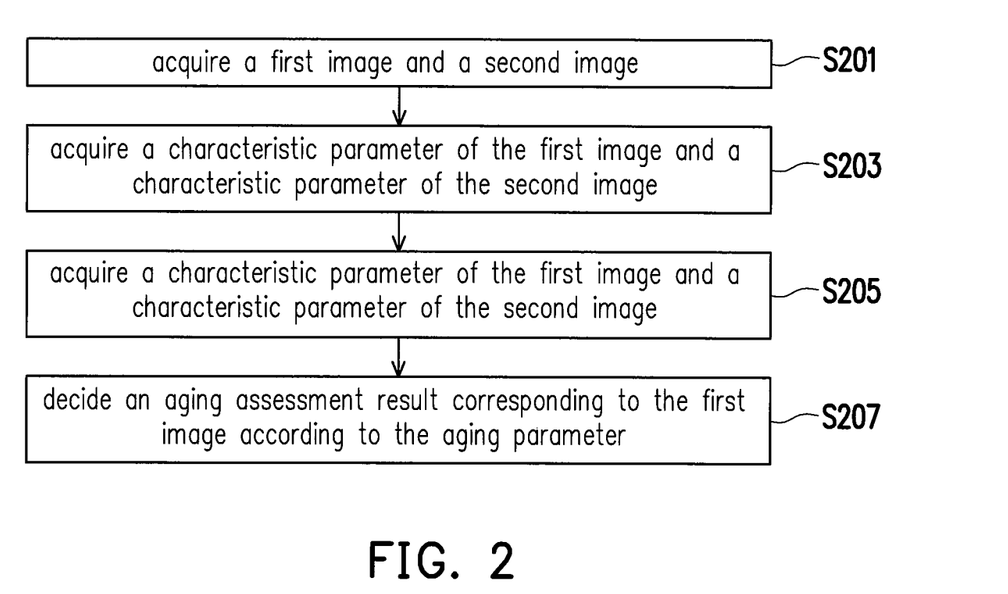
FIG. 2 is a flowchart of a skin aging state assessment method according to an embodiment of the invention.

FIG. 2 is a flowchart of the skin aging state assessment method according to an embodiment of the invention.

Referring to FIG. 2, in Step S201, the image acquisition module 124 acquires a first image and a second image. Then, in Step S203, the characteristic parameter acquisition module 121 acquires a characteristic parameter of the first image and a characteristic parameter of the second image. The first image and the second image are two images captured at two different times, but a subject in the first image is the same as that in the second image. In an embodiment, the first image and the second image may at least respectively include a face region of the subject. However, in another embodiment, the first image and the second image may respectively include the face region and a neck region of the subject. In the embodiment described above, the first image and the second image are acquired via the image acquisition apparatus 130 and then stored in the storage device 120 by the processor 110. The image acquisition module 124 may acquire the first image and the second image from the storage device 120. However, the first image and the second image may also be acquired via different image acquisition apparatuses of different electronic devices. The invention is not intended to limit how the first image and the second image are acquired. For example, the second image may be captured via the image acquisition apparatus of another electronic device, which is different from the electronic device 100, and then be acquired by the image acquisition module 124 of the electronic device 100 to be stored in the storage device 120.

After the image acquisition module 124 acquires the images of the subject, the characteristic parameter acquisition module 121 performs an analysis operation on the acquired images to generate the characteristic parameters of the acquired images.

An acquisition time of the first image is later than an acquisition time of the second image. The acquisition time refers to the time when the image is captured. For example, the image acquisition apparatus 130 captures an image of the subject at a certain time to generate the first image, and the characteristic parameter acquisition module 121 analyzes the first image to generate the characteristic parameter corresponding to the first image. The processor 110 may store the characteristic parameter corresponding to the first image in the storage device 120. Likewise, before generating the first image, the image acquisition apparatus 130 may capture images of the subject at different times to generate multiple images. The characteristic parameter acquisition module 121 then respectively performs the analysis operation on these images to generate the characteristic parameters corresponding to these images, and stores the characteristic parameters corresponding to these images in the storage device 120. In this embodiment, when acquiring the characteristic parameter corresponding to the first image, the image acquisition module 124 may select one of the images in the storage device 120 as the second image, for the characteristic parameter acquisition module 121 to directly acquire the characteristic parameter corresponding to the second image. A time difference between the acquisition time of the first image and the acquisition time of the second image needs to meet a preset value. That is, the time difference between the acquisition time of the first image and the acquisition time of the second image needs to be equal to or greater than the preset value. The preset value may be one month or one year, for example, but the invention is not intended to limit the setting value of the preset value.

Moreover, in another embodiment, when the image acquisition module 124 acquires the first image, the characteristic parameter acquisition module 121 may perform the analysis operation on the first image to acquire the characteristic parameter corresponding to the first image, and in the meantime, the characteristic parameter acquisition module 121 may also acquire the second image from the storage device 120 and perform the analysis operation on the second image to acquire the characteristic parameter corresponding to the second image. In this embodiment, the characteristic parameter generated by the characteristic parameter acquisition module 121 by performing the analysis operation includes a wrinkle ratio, an age spot ratio, and a sag parameter. Details of the analysis operation are described in the following embodiment.

Thereafter, in Step S205, the aging assessment module 122 acquires an aging parameter according to the characteristic parameter of the first image and the characteristic parameter of the second image. More specifically, the aging assessment module 122 calculates a difference between a wrinkle ratio of the first image and a wrinkle ratio of the second image to acquire a wrinkle difference parameter, calculates an age spot ratio of the first image and an age spot ratio of the second image to acquire an age spot difference parameter, and calculates a sag parameter of the first image and a sag parameter of the second image to acquire a sag difference parameter. Then, the aging assessment module 122 acquires the aging parameter according to the wrinkle difference parameter, the age spot difference parameter, and the sag difference parameter. For example, the aging assessment module 122 calculates a product of the wrinkle difference parameter, the age spot difference parameter, and the sag difference parameter to generate the aging parameter.

Next, in Step S207, the aging assessment module 122 decides an aging assessment result corresponding to the first image according to the aging parameter. The aging assessment module 122 may decide an aging speed level according to the aging parameter to serve as the aging assessment result corresponding to the first image. For example, the aging assessment module 122 may preset a plurality of preset conditions to correspond to a plurality of aging speed levels. For example, in this embodiment, the electronic device 100 sets every five years as a level starting from the age of twenty, which is the age of adulthood. One corresponding preset condition is stored for each level, which includes three range conditions, i.e., minimum value range, intermediate value range, and maximum value range, of each level, and the aging speed includes three levels, i.e., slow, medium, and fast. The minimum value range corresponds to the slow level, the intermediate value range corresponds to the medium level, and the maximum value range corresponds to the fast level. After the aging assessment module 122 calculates the aging parameter of the user, the aging assessment module 122 matches the aging parameter of the user to the preset conditions stored in the aging assessment module 122 to assess the degree of aging of the user. That is, the aging assessment module 122 looks up a plurality of preset conditions in the level corresponding to the age of the user according to the age of the user. If the aging parameter falls in the minimum value range of this level, the aging assessment module 122 decides that the aging assessment result corresponding to the first image is slow; if the aging parameter falls in the intermediate value range of this level, the aging assessment module 122 decides that the aging assessment result corresponding to the first image is medium; and if the aging parameter falls in the maximum value range of this level, the aging assessment module 122 decides that the aging assessment result corresponding to the first image is fast.

At last, the information providing module 123 outputs prompt information according to the aging assessment result decided by the aging assessment module 122. For example, the information providing module 123 may output prompt information corresponding to the aging speed level. The prompt information indicates the aging speed of the first image with respect to the second image.

As described above, the characteristic parameter that the characteristic parameter acquisition module 121 generates by performing the analysis operation may include the wrinkle ratio, the age spot ratio, and the sag parameter. Several embodiments are provided hereinafter to explain in detail how to acquire the aforementioned characteristic parameters.

Figure 3:
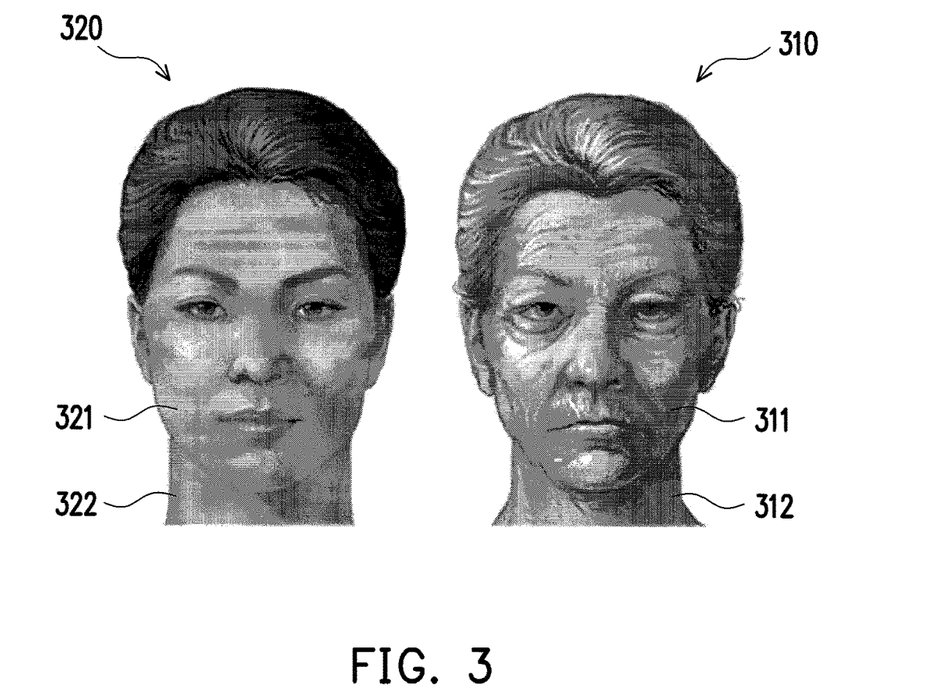
FIG. 3 is a view of acquiring a wrinkle ratio according to an embodiment of the invention.

FIG. 3 is a view of acquiring the wrinkle ratio according to an embodiment of the invention. In the embodiment of FIG. 3, it is assumed that the first image is an image 310 and the second image is an image 320, and the acquisition time of the image 310 is later than the acquisition time of the image 320.

Referring to FIG. 3, after acquiring the image 320, the characteristic parameter acquisition module 121 performs the analysis operation on the image 320 to acquire the wrinkle ratio (also referred to as second wrinkle ratio) corresponding to the image 320. More specifically, the characteristic parameter acquisition module 121 acquires the number of wrinkles of a face region 321 in the image 320 and a face area of the face region 321, and calculates a ratio of the number of wrinkles of the face region 321 to the face area of the face region 321 to acquire the wrinkle ratio of the image 320. Then, the processor 110 may store the second wrinkle ratio in the storage device 120. That is, in an embodiment, the second wrinkle ratio may be the wrinkle ratio of the face region 321 in the image 320.

However, in another embodiment, the characteristic parameter acquisition module 121 may also acquire the number of wrinkles of a neck region 322 in the image 320 and a neck area of the neck region 322. The characteristic parameter acquisition module 121 calculates a sum of the number of wrinkles of the face region 321 and the number of wrinkles of the neck region 322 in the image 320 to acquire a total wrinkle number, and calculates a sum of the face area of the face region 321 and the neck area of the neck region 322 to acquire a total region area. Next, the characteristic parameter acquisition module 121 calculates a percentage ratio of the total wrinkle number and the total region area to acquire the wrinkle ratio corresponding to the image 320. Thereafter, the processor 110 may store the first wrinkle ratio in the storage device 120. That is, the first wrinkle ratio may be the wrinkle ratio of the face region and the neck region in the image 320. Particularly, the ratio may be a value greater than or equal to 0 and smaller than or equal to 100. There are existing techniques available for identifying the wrinkles, the face region, and the neck region in the image and thus they are not repeated hereinafter.

After acquiring the image 310, the characteristic parameter acquisition module 121 performs the analysis operation on the face region 311 and the neck region 312 in the image 310 to acquire the wrinkle ratio (also referred to as first wrinkle ratio) corresponding to the image 310. Thereafter, the processor 110 may store the first wrinkle ratio in the storage device 120. The characteristic parameter acquisition module 121 acquires the first wrinkle ratio in the same manner as the second wrinkle ratio and thus it is not repeated hereinafter. In an embodiment, the first wrinkle ratio may be the wrinkle ratio of the face region 321 in the image 320. However, in another embodiment, the first wrinkle ratio may be the wrinkle ratio of the face region and the neck region in the image 320. Because the first wrinkle ratio and the second wrinkle ratio that the characteristic parameter acquisition module 121 acquires according to the image 310 and the image 320 are stored in the storage device 120, the aging assessment module 122 may read the first wrinkle ratio and the second wrinkle ratio and calculate the difference therebetween to acquire the wrinkle difference parameter.

Figure 4:
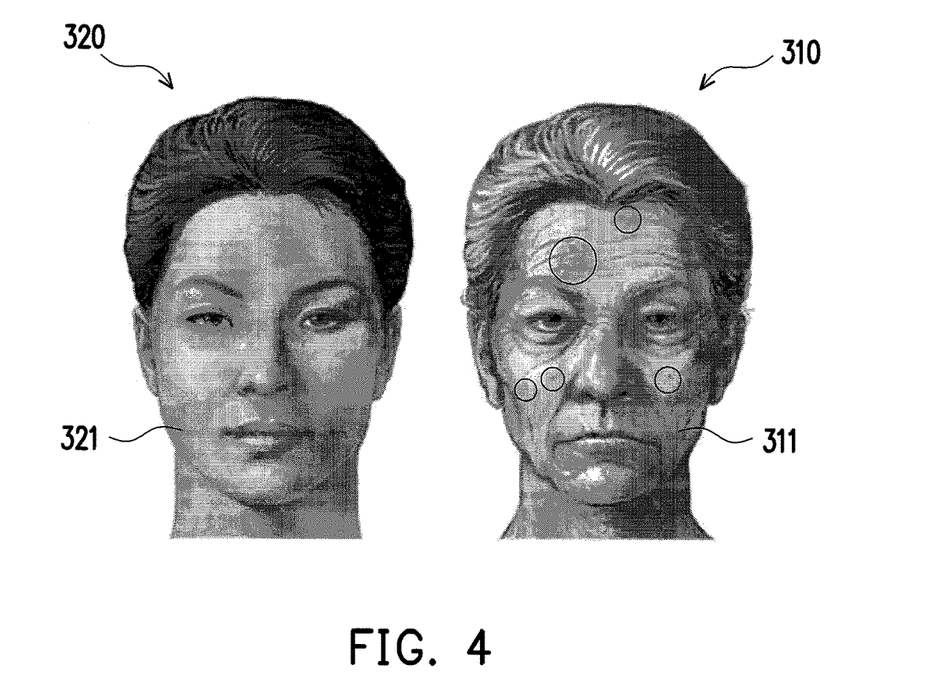
FIG. 4 is a view of acquiring an age spot ratio according to an embodiment of the invention.

FIG. 4 is a view of acquiring the age spot ratio according to an embodiment of the invention. FIG. 4 is described also based on the image 310 and the image 320 of FIG. 3.

Referring to FIG. 4, after acquiring the image 320, the characteristic parameter acquisition module 121 performs the analysis operation on the image 320 to acquire the age spot ratio (also referred to as second age spot ratio) corresponding to the image 320. More specifically, the characteristic parameter acquisition module 121 acquires the age spot area of the face region 321 in the image 320, and calculates a percentage ratio of the age spot area of the face region 321 to the face area of the face region 321 to acquire the age spot ratio of the image 320. Then, the processor 110 may store the second age spot ratio in the storage device 120.

After acquiring the image 310, the characteristic parameter acquisition module 121 performs the analysis operation on face region 311 and the neck region 312 in the image 310 to acquire the age spot ratio (also referred to as first age spot ratio) corresponding to the image 310. Then, the processor 110 may store the second age spot ratio in the storage device 120. The characteristic parameter acquisition module 121 acquires the first age spot ratio in the same manner as the second age spot ratio and thus it is not repeated hereinafter. Particularly, the ratio may be a value greater than or equal to 0 and smaller than or equal to 100. There are existing techniques available for identifying the age spot in the image and thus they are not repeated hereinafter. Because the first age spot ratio and the second age spot ratio that the characteristic parameter acquisition module 121 acquires according to the image 310 and the image 320 are stored in the storage device 120, the aging assessment module 122 may read the first age spot ratio and the second age spot ratio and calculate the difference therebetween to acquire the age spot difference parameter.

Figure 5:
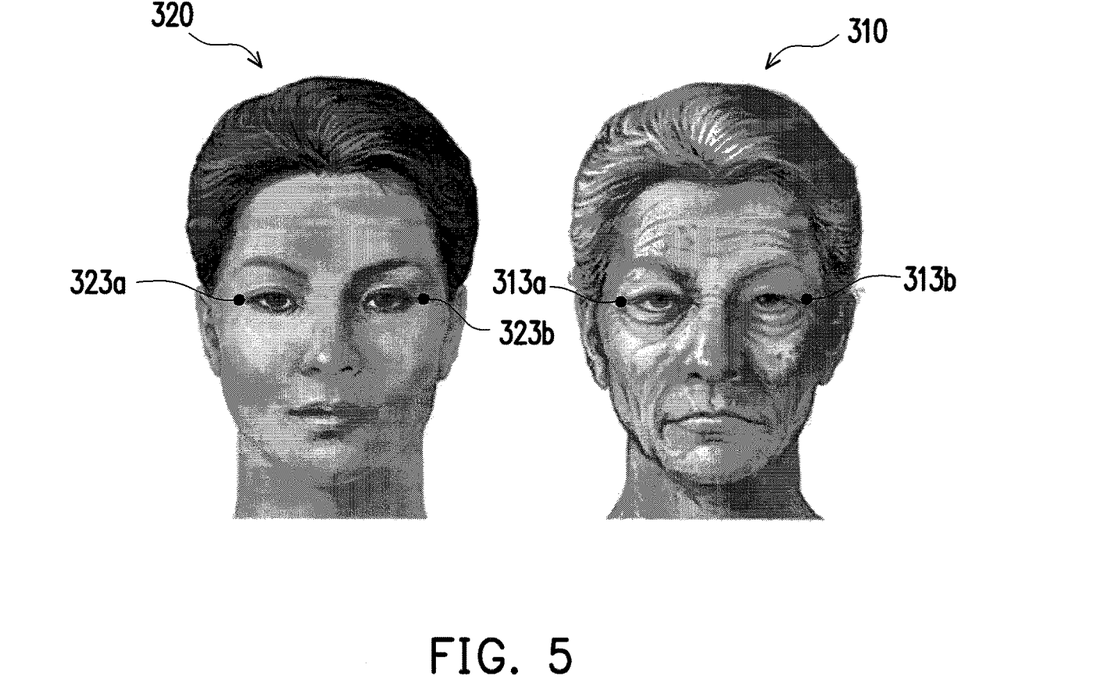
FIG. 5 is a view of acquiring a sag parameter according to an embodiment of the invention.

FIG. 5 is a view of acquiring the sag parameter according to an embodiment of the invention. FIG. 5 is described also based on the image 310 and the image 320 of FIG. 3.

Referring to FIG. 5, after acquiring the image 320, the characteristic parameter acquisition module 121 performs the analysis operation on the image 320 to acquire the sag parameter (also referred to as second sag parameter) corresponding to the image 320. More specifically, the characteristic parameter acquisition module 121 acquires an eye corner endpoint position in the image 320 to acquire the sag parameter of the image 320. For example, after acquiring the image 320, the processor 120 may detect and analyze a plurality of characteristic points in the image 320 by a specific face detection technique, and each of the characteristic points has a specific number. That is, in different face images, the characteristic points corresponding to the same position have the same specific number. In addition, the processor 120 may further assign a coordinate, e.g., (x,y), to each of the characteristic points based on a coordinate system. In other words, the eye corner endpoint may be one of multiple characteristic points of the image, and the eye corner endpoint position may be represented by a coordinate. In an embodiment, the characteristic parameter acquisition module 121 may acquire the x coordinate of an eye corner endpoint position 323a or the x coordinate of an eye corner endpoint position 323b in the image 320 to serve as the second sag parameter. Moreover, the characteristic parameter acquisition module 121 may acquire the y coordinate of the eye corner endpoint position 323a or the y coordinate of the eye corner endpoint position 323b in the image 320 to serve as a fourth sag parameter. However, in another embodiment, the characteristic parameter acquisition module 121 may acquire an average of the x coordinate of the eye corner endpoint position 323a and the x coordinate of the eye corner endpoint position 323b in the image 320 to serve as the second sag parameter, and an average of the y coordinate of the eye corner endpoint position 323a and the y coordinate of the eye corner endpoint position 323b to serve as the fourth sag parameter. Then, the processor 110 may store the second sag parameter and the fourth sag parameter in the storage device 120. There are existing face detection techniques available for identifying the characteristic points and the characteristic point coordinates in the image and thus they are not repeated hereinafter. After acquiring the image 310, the characteristic parameter acquisition module 121 performs the analysis operation on the image 310 to acquire the sag parameters (also referred to as first sag parameter and third sag parameter) corresponding to the image 310. The characteristic parameter acquisition module 121 acquires the first sag parameter and the third sag parameter in the same manner as the second sag parameter and the fourth sag parameter and thus it is not repeated hereinafter. In an embodiment, the characteristic parameter acquisition module 121 may acquire the x coordinate of an eye corner endpoint position 313a or the x coordinate of an eye corner endpoint position 313b in the image 310 to serve as the first sag parameter. Moreover, the characteristic parameter acquisition module 121 may acquire the y coordinate of the eye corner endpoint position 313a or the y coordinate of the eye corner endpoint position 313b in the image 310 to serve as the third sag parameter. However, in another embodiment, the characteristic parameter acquisition module 121 may acquire an average of the y coordinate of the eye corner endpoint position 313a and the x coordinate of the eye corner endpoint position 313b in the image 320 to serve as the first sag parameter, and an average of the y coordinate of the eye corner endpoint position 313a and the y coordinate of the eye corner endpoint position 313b to serve as the third sag parameter. Then, the processor 110 may store the first sag parameter and the third sag parameter in the storage device 120. It should be noted that the specific number of the eye corner endpoint position 313a of the image 310 is the same as the specific number of the eye corner endpoint position 323a of the image 320, and the specific number of the eye corner endpoint position 313b of the image 310 is the same as the specific number of the eye corner endpoint position 323b of the image 320.

Because the first sag parameter, the second sag parameter, the third sag parameter, and the fourth sag parameter that the characteristic parameter acquisition module 121 acquires according to the image 310 and the image 320 are stored in the storage device 120, the aging assessment module 122 may read the first sag parameter, the second sag parameter, the third sag parameter, and the fourth sag parameter and calculate the difference therebetween to acquire the sag difference parameter. More specifically, the sag difference parameter is calculated mainly for determining whether the eye corner endpoint positions 313a and 323a and/or the eye corner endpoint positions 313b and 323b in the image 310 and the image 320 have sagged or become loose, so as to assess the degree of aging. Therefore, in this embodiment, the aging assessment module 122 calculates a displacement of the eye corner endpoint positions 313a and 323a and/or the eye corner endpoint positions 313b and 323b according to the first sag parameter, the second sag parameter, the third sag parameter, and the fourth sag parameter. The displacement is the sag difference parameter. The displacement calculated according to the first sag parameter, the second sag parameter, the third sag parameter, and the fourth sag parameter may be acquired by calculating a distance between two existing points on a coordinate plane, and thus it is not repeated hereinafter.

In addition to calculating the displacement, the aging assessment module 122 determines whether the eye corner endpoint positions 313a and 323a and/or the eye corner endpoint positions 313b and 323b have sagged or become loose according to the first sag parameter, the second sag parameter, the third sag parameter, and the fourth sag parameter. For example, the aging assessment module 122 assesses whether the eye corner endpoint has moved outward according to the difference between the first sag parameter and the third sag parameter. If the eye corner endpoint has moved outward, the aging assessment module 122 determines that the eye has become loose and sets the sag difference parameter to a positive value. However, if the eye corner endpoint has moved inward, the aging assessment module 122 determines that the eye has become firm and sets the sag difference parameter to a negative value.

Figure 6:
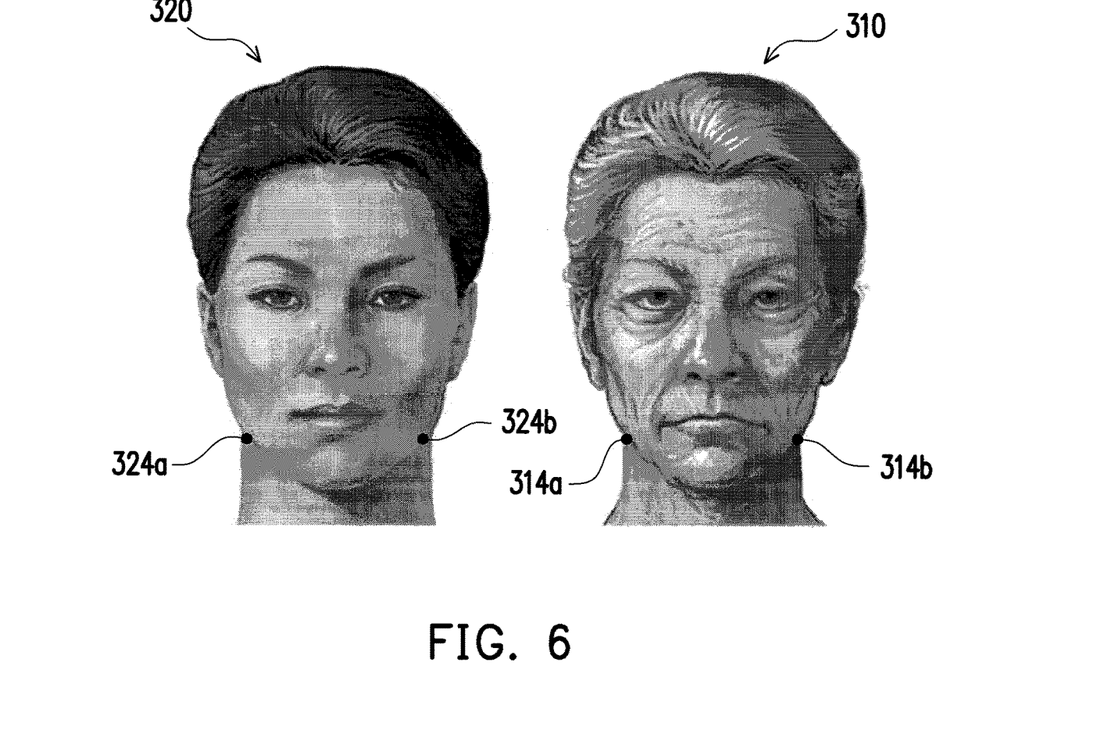
FIG. 6 is a view of acquiring a sag parameter according to another embodiment of the invention.

FIG. 6 is a view of acquiring the sag parameter according to another embodiment of the invention. FIG. 6 is described also based on the image 310 and the image 320 of FIG. 3. In both FIG. 6 and FIG. 5, the sag parameter is acquired according to specific characteristic points in the images.

Referring to FIG. 6, like the embodiment of FIG. 5, after acquiring the image 320, the characteristic parameter acquisition module 121 performs the analysis operation on the image 320 to acquire the second sag parameter and the fourth sag parameter. What differentiates the embodiment of FIG. 6 from the embodiment of FIG. 5 is that, in the embodiment of FIG. 6, the characteristic parameter acquisition module 121 acquires the sag parameter according to a cheek endpoint position. The cheek endpoint is one of the characteristic points of the image, and the cheek endpoint position may be represented by a coordinate. In an embodiment, the characteristic parameter acquisition module 121 may acquire the x coordinate of a cheek endpoint position 324a or the x coordinate of a cheek endpoint position 324b in the image 320 to serve as the second sag parameter. Moreover, the characteristic parameter acquisition module 121 may acquire the y coordinate of the cheek endpoint position 324a or the y coordinate of the cheek endpoint position 324b in the image 320 to serve as the fourth sag parameter. However, in another embodiment, the characteristic parameter acquisition module 121 may acquire an average of the x coordinate of the cheek endpoint position 324a and the x coordinate of the cheek endpoint position 324b in the image 320 to serve as the second sag parameter, and an average of the y coordinate of the cheek endpoint position 324a and the y coordinate of the cheek endpoint position 324b to serve as the fourth sag parameter. Then, the processor 110 may store the second sag parameter and the fourth sag parameter in the storage device 120.

After acquiring the image 310, in an embodiment, the characteristic parameter acquisition module 121 may acquire the x coordinate of a cheek endpoint position 314a or the x coordinate of a cheek endpoint position 314b in the image 310 to serve as the first sag parameter. Moreover, the characteristic parameter acquisition module 121 may acquire the y coordinate of the cheek endpoint position 314a or the y coordinate of the cheek endpoint position 314b in the image 310 to serve as the third sag parameter. However, in another embodiment, the characteristic parameter acquisition module 121 may acquire an average of the x coordinate of the cheek endpoint position 314a and the x coordinate of the cheek endpoint position 314b in the image 310 to serve as the first sag parameter. Moreover, the characteristic parameter acquisition module 121 may acquire an average of the y coordinate of the cheek endpoint position 314a and the y coordinate of the cheek endpoint position 314b in the image 310 to serve as the third sag parameter. Then, the processor 110 may store the first sag parameter and the third sag parameter in the storage device 120. It should be noted that the specific number of the cheek endpoint position 314a of the image 310 is the same as the specific number of the cheek endpoint position 324a of the image 320, and the specific number of the cheek endpoint position 314b of the image 310 is the same as the specific number of the cheek endpoint position 324b of the image 320. After acquiring the first sag parameter, the second sag parameter, the third sag parameter, and the fourth sag parameter, the aging assessment module 122 calculates the sag difference parameter according to the first sag parameter, the second sag parameter, the third sag parameter, and the fourth sag parameter. The aging assessment module 122 acquires the sag difference parameter in the same manner as the disclosure of FIG. 5 and thus it is not repeated hereinafter.

Figure 7:
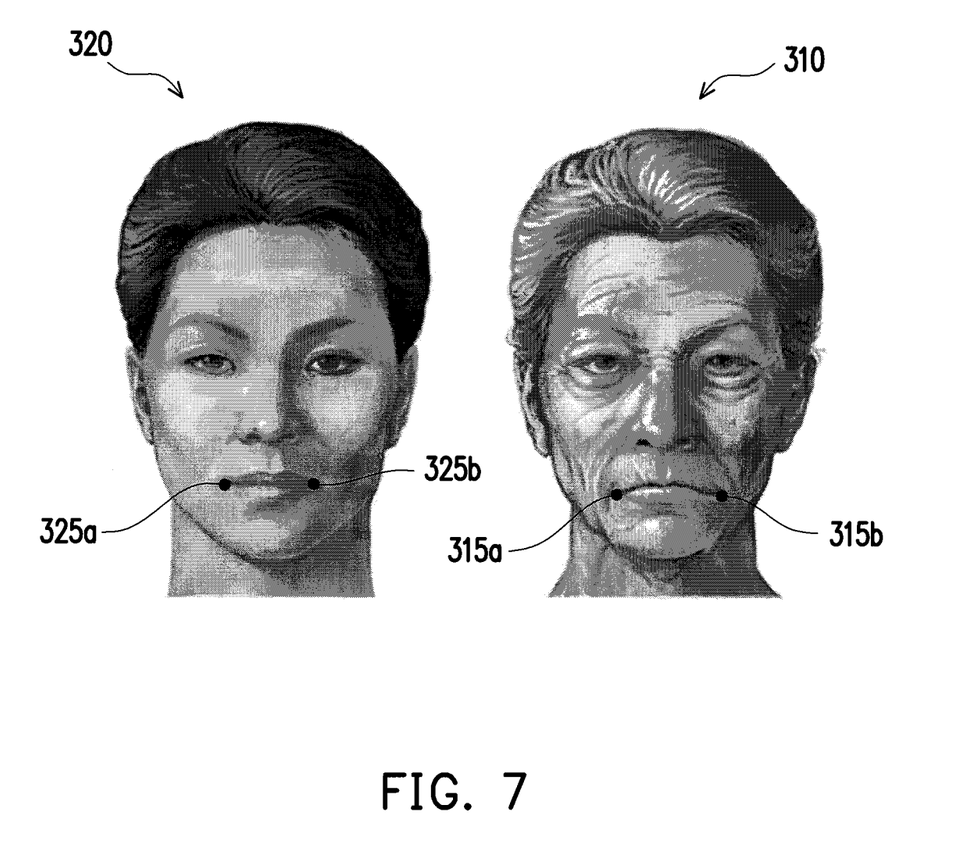
FIG. 7 is a view of acquiring a sag parameter according to yet another embodiment of the invention.

FIG. 7 is a view of acquiring the sag parameter according to yet another embodiment of the invention. FIG. 7 is described also based on the image 310 and the image 320 of FIG. 3. In FIG. 7, FIG. 5, and FIG. 6, the sag parameter is acquired according to specific characteristic points in the images.

Referring to FIG. 7, like the embodiments of FIG. 5 and FIG. 6, after acquiring the image 320, the characteristic parameter acquisition module 121 performs the analysis operation on the image 320 to acquire the second sag parameter and the fourth sag parameter. What differentiates the embodiment of FIG. 7 from the embodiments of FIG. 5 and FIG. 6 is that, in the embodiment of FIG. 7, the characteristic parameter acquisition module 121 acquires the sag parameter according to a lip corner endpoint position. The lip corner endpoint is one of the characteristic points of the image, and the lip corner endpoint position may be represented by a coordinate. In an embodiment, the characteristic parameter acquisition module 121 may acquire the x coordinate of a lip corner endpoint position 325a or the x coordinate of a lip corner endpoint position 325b in the image 320 to serve as the second sag parameter, and acquire the y coordinate of the lip corner endpoint position 325a or the y coordinate of the lip corner endpoint position 325b in the image 320 to serve as the fourth sag parameter. However, in another embodiment, the characteristic parameter acquisition module 121 may acquire an average of the x coordinate of the lip corner endpoint position 325a and the x coordinate of the lip corner endpoint position 325b in the image 320 to serve as the second sag parameter, and an average of the y coordinate of the lip corner endpoint position 325a and the y coordinate of the lip corner endpoint position 325b in the image 320 to serve as the fourth sag parameter. Then, the processor 110 may store the second sag parameter and the fourth sag parameter in the storage device 120.

After acquiring the image 310, in an embodiment, the characteristic parameter acquisition module 121 may acquire the x coordinate of a lip corner endpoint position 315a or the x coordinate of a lip corner endpoint position 315b in the image 310 to serve as the first sag parameter, and acquire the y coordinate of the lip corner endpoint position 315a or the y coordinate of the lip corner endpoint position 315b in the image 310 to serve as the third sag parameter. However, in another embodiment, the characteristic parameter acquisition module 121 may acquire an average of the x coordinate of the lip corner endpoint position 315a and the x coordinate of the lip corner endpoint position 315b in the image 310 to serve as the first sag parameter, and an average of the y coordinate of the lip corner endpoint position 315a and the y coordinate of the lip corner endpoint position 315b in the image 310 to serve as the third sag parameter. Then, the processor 110 may store the first sag parameter and the third sag parameter in the storage device 120. It should be noted that the specific number of the lip corner endpoint position 315a of the image 310 is the same as the specific number of the lip corner endpoint position 325a of the image 320, and the specific number of the lip corner endpoint position 315b of the image 310 is the same as the specific number of the lip corner endpoint position 325b of the image 320. After acquiring the first sag parameter, the second sag parameter, the third sag parameter, and the fourth sag parameter, the aging assessment module 122 calculates the sag difference parameter according to the first sag parameter, the second sag parameter, the third sag parameter, and the fourth sag parameter. The aging assessment module 122 acquires the sag difference parameter in the same manner as the disclosure of FIG. 5 and thus it is not repeated hereinafter.

In yet another embodiment of the disclosure, the aging assessment module 122 comprehensively assesses the sag difference parameter according to the first sag parameters, the second sag parameters, the third sag parameters, and the fourth sag parameters that the characteristic parameter acquisition module 121 respectively acquires with respect to the eye corner endpoints, the cheek endpoints, and the lip corner endpoints in FIG. 5, FIG. 6, and FIG. 7. More specifically, the aging assessment module 122 calculates a first sag difference parameter with respect to the first sag parameter, the second sag parameter, the third sag parameter, and the fourth sag parameter of the eye corner endpoint; calculates a second sag difference parameter with respect to the first sag parameter, the second sag parameter, the third sag parameter, and the fourth sag parameter of the cheek endpoint; and calculates a third sag difference parameter with respect to the first sag parameter, the second sag parameter, the third sag parameter, and the fourth sag parameter of the lip corner endpoint. Further, the aging assessment module 122 calculates a sum of the first sag difference parameter, the second sag difference parameter, and the third sag difference parameter to acquire a total sag difference parameter. In addition, when calculating the aging parameter of the user, the aging assessment module 122 uses the total sag difference parameter as one of the bases for generating the aging parameter.

To sum up, in the skin aging state assessment method of the invention, the skin aging parameter of the user is acquired according to two images that are captured at different times, and the skin aging assessment result of the user is decided according to the skin aging parameter, so as to provide corresponding prompt information. Also, according to the skin aging state assessment method of the invention, the aging speed level may be decided based on the skin aging parameter, such that the user may know the skin aging condition or aging speed.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. A skin aging state assessment method, comprising:
   acquiring a first image and a second image;
   acquiring a characteristic parameter of the first image and a characteristic parameter of the second image;
   acquiring an aging parameter according to the characteristic parameter of the first image and the characteristic parameter of the second image; and
   deciding an aging assessment result corresponding to the first image according to the aging parameter.

2. The skin aging state assessment method according to claim 1, wherein the characteristic parameter of the first image and the characteristic parameter of the second image respectively comprise a wrinkle ratio, an age spot ratio, and a sag parameter, wherein acquiring the aging parameter according to the characteristic parameter of the first image and the characteristic parameter of the second image comprises:
   calculating a difference between the wrinkle ratio of the first image and the wrinkle ratio of the second image to acquire a wrinkle difference parameter;
   calculating a difference between the age spot ratio of the first image and the age spot ratio of the second image to acquire an age spot difference parameter;
   calculating a difference between the sag parameter of the first image and the sag parameter of the second image to acquire a sag difference parameter; and
   calculating a product of the wrinkle difference parameter, the age spot difference parameter, and the sag difference parameter to acquire the aging parameter.

3. The skin aging state assessment method according to claim 1, wherein deciding the aging assessment result corresponding to the first image according to the aging parameter comprises:
   comparing the aging parameter with a plurality of preset conditions to decide an aging speed level as the aging assessment result corresponding to the first image.

4. The skin aging state assessment method according to claim 3, further comprising:
   providing prompt information corresponding to the aging speed level.

5. The skin aging state assessment method according to claim 1, further comprising:
   acquiring the first image; and
   acquiring the second image,
   wherein an acquisition time of the first image is later than an acquisition time of the second image, and a time difference between the acquisition time of the first image and the acquisition time of the second image meets a preset value.

6. The skin aging state assessment method according to claim 1, wherein acquiring the characteristic parameter of the first image and the characteristic parameter of the second image comprises:
   performing an analysis operation on the first image to generate the characteristic parameter of the first image; and
   performing the analysis operation on the second image to generate the characteristic parameter of the second image,
   wherein the analysis operation comprises:
   acquiring a face wrinkle number and a face area of an image; and
   calculating a ratio of the face wrinkle number to the face area to acquire a wrinkle ratio of the image as a characteristic parameter of the image.

7. The skin aging state assessment method according to claim 6, wherein the analysis operation further comprises:
   acquiring a neck wrinkle number and a neck area of the image;
   calculating a sum of the face wrinkle number and the neck wrinkle number to acquire a total wrinkle number;
   calculating a sum of the face area and the neck area to acquire a total region area; and
   calculating a ratio of the total wrinkle number to the total region area to acquire the wrinkle ratio of the image as the characteristic parameter of the image.

8. The skin aging state assessment method according to claim 6, wherein the analysis operation further comprises:
   acquiring an age spot area of the image; and calculating a ratio of the age spot area to the face area to acquire an age spot ratio of the image as the characteristic parameter of the image.

9. The skin aging state assessment method according to claim 8, wherein the analysis operation further comprises:
acquiring a sag parameter of the image according to an eye corner endpoint position of the image as the characteristic parameter of the image.

10. The skin aging state assessment method according to claim 8, wherein the analysis operation further comprises:
acquiring a sag parameter of the image according to a cheek endpoint position of the image as the characteristic parameter of the image.

11. An electronic device, comprising:
a memory storing a plurality of modules; and
a processor coupled to the memory and accessing and executing the modules stored in the memory so as to perform:
acquiring a first image and a second image;
acquiring a characteristic parameter of the first image and a characteristic parameter of the second image; and
acquiring an aging parameter according to the characteristic parameter of the first image and the characteristic parameter of the second image, and deciding an aging assessment result corresponding to the first image according to the aging parameter.

12. The electronic device according to claim 11, wherein the characteristic parameter of the first image and the characteristic parameter of the second image respectively comprise a wrinkle ratio, an age spot ratio, and a sag parameter, wherein when the processor acquires the aging parameter according to the characteristic parameter of the first image and the characteristic parameter of the second image, the processor:
calculates a difference between the wrinkle ratio of the first image and the wrinkle ratio of the second image to acquire a wrinkle difference parameter;
calculates a difference between the age spot ratio of the first image and the age spot ratio of the second image to acquire an age spot difference parameter;
calculates a difference between the sag parameter of the first image and the sag parameter of the second image to acquire a sag difference parameter; and
calculates a product of the wrinkle difference parameter, the age spot difference parameter, and the sag difference parameter to acquire the aging parameter.

13. The electronic device according to claim 11, wherein when the processor decides the aging assessment result corresponding to the first image according to the aging parameter, the processor compares the aging parameter with a plurality of preset conditions to decide an aging speed level as the aging assessment result corresponding to the first image.

14. The electronic device according to claim 13, wherein the processor further performs:
providing prompt information corresponding to the aging speed level.

15. The electronic device according to claim 11, further comprising:
a camera coupled to the processor, wherein the camera is configured to acquire the first image and the second image,
wherein an acquisition time of the first image is later than an acquisition time of the second image, and a time difference between the acquisition time of the first image and the acquisition time of the second image meets a preset value.

16. The electronic device according to claim 11, wherein the processor performs an analysis operation on the first image to generate the characteristic parameter of the first image, and performs the analysis operation on the second image to generate the characteristic parameter of the second image,
wherein when the processor performs the analysis operation, the processor:
acquires a face wrinkle number and a face area of an image; and
calculates a ratio of the face wrinkle number to the face area to acquire a wrinkle ratio of the image as a characteristic parameter of the image.

17. The electronic device according to claim 16, wherein when the processor performs the analysis operation, the processor further:
acquires a neck wrinkle number and a neck area of the image;
calculates a sum of the face wrinkle number and the neck wrinkle number to acquire a total wrinkle number;
calculates a sum of the face area and the neck area to acquire a total region area; and
calculates a ratio of the total wrinkle number to the total region area to acquire the wrinkle ratio of the image as the characteristic parameter of the image.

18. The electronic device according to claim 16, wherein when the processor performs the analysis operation, the processor further:
acquires an age spot area of the image; and
calculates a ratio of the age spot area to the face area to acquire an age spot ratio of the image as the characteristic parameter of the image.

19. The electronic device according to claim 18, wherein when the processor performs the analysis operation, the processor further acquires a sag parameter of the image according to an eye corner endpoint position of the image as the characteristic parameter of the image.

20. The electronic device according to claim 18, wherein when the processor performs the analysis operation, the processor further acquires a sag parameter of the image according to a cheek endpoint position of the image as the characteristic parameter of the image.

* * * * *